United States Patent [19]

Winkler et al.

[11] Patent Number: 5,645,838
[45] Date of Patent: Jul. 8, 1997

[54] ASSAY FOR CHAGAS' DISEASE AND REAGENTS FOR ITS USE

[75] Inventors: Martin A. Winkler, Lindenhurst; Alfred A. Pan, Grayslake, both of Ill.

[73] Assignee: Abbott Laboratories, Abbott Park, Ill.

[21] Appl. No.: 450,442

[22] Filed: May 25, 1995

Related U.S. Application Data

[62] Division of Ser. No. 275,086, Jul. 13, 1994, Pat. No. 5,550,027, which is a continuation of Ser. No. 911,590, Jul. 10, 1992, abandoned.

[51] Int. Cl.$^6$ .............................. A61K 39/02; C07K 1/00
[52] U.S. Cl. ........................................ 424/269.1; 530/395
[58] Field of Search .......................... 424/269.1; 530/395

[56] References Cited

FOREIGN PATENT DOCUMENTS

76093/87   2/1988   Austria .

OTHER PUBLICATIONS

G.A. Schmunis, et al., "Trypanosoma cruzi, The Etiological Agent of Chagas' Disease: Status in the Blood Supply in Endemic and Nonendemic Countries," *Transfusion* 31(6): 547–557 (1991).
Anonymous, "Control of Chagas Disease: Report of a WHO Expert Committee," WHO Technical Report Series 1991, 811:1–93 WHO, Geneva (1991).
S. Kingman, "South America Declares War on Chagas Disease," *New Scientist* 132:16–17 (19 October 1991).
N.C. Woody, et al., "American Trypanomomiasis (Chagas' Disease): First Indigenous Case in the United States," *JAMA* 159(7):676–677 (1985).
R.J. Schiffler, et al., "Indigenous Chagas' Disease (Ameican Trypanosomiasis) in California," *J.A.M.A.* 251(22):2983–2984 (1984).
J.D. Pearlman, "Chagas' Disease in Northern California," *Am. J. Med.* 75:1057–1060 (1983).
T.R. Navin, et al., "Human and Sylvatic Trypanosoma cruzi Infection in California," *Am. J. Public Health* 75(4):366–369 (1985).
L.V. Kirchhoff, et al., "Chagas' Disease in Latin American Immigrants," *JAMA* 254(21):3058–3060 (1985).
L.V. Krichhoff, et al., "American Trypanosomiasis (Chagas' Disease) in Central American Immigrants," *Am. J. Med.* 82(915–920) (1987).
A. Skolnick, "Deferral Aims to Deter Chagas' Parasite," *JAMA* 265(2):173 (Jan., 1991).
P. Kerndt, et al., "Trypanosoma cruzi Antibody Among Blood Donors in Los Angeles, California", *Transfusion* 28 (Supplement):31S, Abstract No. S108 (1988).
P.R. Kerndt, et al., "Prevelance of Antibody to Trypanosoma cruzi Among Blood Donors in Los Angeles, California" *Transufison* 31(9):814–818 (1991).
P.O. Pehrson, et al., "Asymopomatic Congenital Chagas' Disease in a 5 Year Old Child," *Scan. J. Inf. Dis.* 3:307–308 (1981).

A. Skolnick, "Does Influx From Endemic Areas Mean More Transfusion–Associated Chagas' Disease?" *JAMA* 262(11):1433 (1989).
P. Nickerson, et al., "Transfusion–Associated Trypanosoma cruzi Infection in a non–endemic area," *Ann. Int. Med.* 111(10):851–853 (1989).
Anonymous, "Parasite T. cruzi in US Blood Supply?" *Clinica* No. 354:16 (Jun. 7, 1989).
L.V. Kirchhoff, "Is Trypanosoma cruzi a New Threat to Our Blood Supply?" *Ann. Int. Med.* 111(10):773–775 (1989).
G. Bonfirm, et al., "Detection of Antibodies to Trypansoma cruzi in Blood Donors," *Abstract of Inter. Soc. ofBlood Trans./Am. Assoc. Blood Banks* Abstract No. S445, (Nov. 10–15, 1990).
I.H. Grant, et al., "Transfusion–Associated Acute Chagas Disease Acquired in the United States," *Ann. Int. Med.* 111(10):849–850 (1989).
M. Boxaca, et al., "HIV–1 Prevelance and the Role of Other Infection Diseases in a Group of Drug Users in Argentina," Track C: Epidemology & Prevention, *Int. Conf. AIDS* Abstract No. 3141 (1991).
A.L. Bittencourt, "Congential Chagas Disease," *Am. J. Dis. Child* 130:97–103 (1976).
Hoff, et al., "Congential Chagas' Disease in an Urgan Population: Investigation of Infected Twins," *Trans. Royal Soc. Trop. Med. and Hygeine* 72(3):247–250 (1978).
M.D. Gudino, et al., Chagas' Disease and Blood Transfusion, in R.G. Westphal, et al., eds., *Emerging Global Patterns in Transfusion Transmitted Infections* pp. 65–68 American Assoc. of Blood Banks, Arlington, VA (1990).
I.G. Kagan, et al., "Studies on Trypanosoma cruzi Isolated in the United States: A Review," *Rev. Biol. Trop.* 14(1):55–73 (1966).
J.C. P.Dias, et al., "Chagas' Disease and Blood Transfusion," *Mem. Inst. Oswaldo Cruz,* Rio de Janiero, Suppl. 79:139–147 (1984).
E.L. Segura, "Xenodiagnosis" in *Chagas' Disease Vectors,* R.R. Brenner, et al., eds., II:41–45, Boca Raton, FL, CRC Press (1987).

(List continued on next page.)

*Primary Examiner*—James C. Housel
*Assistant Examiner*—Jennifer Shaver
*Attorney, Agent, or Firm*—Cheryl L. Becker; Priscilla E. Porembski

[57] ABSTRACT

An assay to confirm the presence of antibodies to *T. cruzi* in a test sample. The assay comprises detecting the presence of antibody to three *T. cruzi* antigens, Gp90, Gp 60/50 and LPPG in a test sample. The presence of antibody in the test sample to at least two of three *T. cruzi* antibodies is indicative of a confirmed reactive sample. Also provided are diagnostic reagents for detection of *T. cruzi,* a process for purifying GP 60/50, a process for linking a protein and LPPG, and diagnostic test kits for use when assaying for antibodies to *T. cruzi.*

1 Claim, 4 Drawing Sheets

OTHER PUBLICATIONS

F. Zicker, et al., "Mass Screening for Trypanosoma cruzi Infections Using the Immunofluorescence, ELISA and Haemagglutination Tests on Serum Samples and on Blood Eluates from Filter–Pater," Bull. of WHO 68(4):465–471 (1990).

M.E. Camargo, et al., "Three Years of Collaboration on the Standardization of Chagas' Disease Serodiagnosis in the America: An Appraisal," PAHO Bull. 20(3):233–244 (1986).

A.A. Pan, et al. "Clinical Evaluation of an EIA for the Sensitive and Specific Detection of Serum Antibody to Iryaconosoma cruzi (Chagas' Disease)," JID 165:585–588 (Mar. 1992).

D.M. Israelski, et al., "Antibody Response and Antigen Recognition in Human Infection With Trypanosoma cruzi," Am. J. Med. Hygiene 39(5):445–455 (1988).

R. Lelchuck, et al., "Immunoglobulin Studies in Serum of patients with American Trypanosomiasis (Chagas' Disease)," Clin. Exp. Immunol. 6:547–555 (1970).

N.H. Vattuone, et al., "Antibody Response and Immunoglobulin Levels in Humans with Acute or Chronic Trypanosoma cruzi Infentions (Chagas' Disease)," Am. J. Trop. Med. Hyg. 76:45–47 (1973).

D.E. Lanar, et al., "Complexity and Content of the DNA and RNA in Trypansoma Cruzi," Molec. and Biochem. Parasit. 3:337–341 (1981).

S.P. Craig, et al., "Trypanosoma (Schizotrypanum) cruzi: Repetitive DNA Sequence Evolution in Three Geographically Distinct Isolates," Comp. Biochem. Physiol. 95B (4):657–662 (1990).

M. Schechter, et al., "Purified Trypanosoma cruzi Specific Glycoprotein for Distriminative Serological Diagnosis of South american Trypanosomiasis (Chagas' Disease)", Lancet 939–941 (Oct. 22, 1983).

L.V. Kirchhoff, et al., "Increased Specificity of Serodiagnosis of Chagas' Disease by Detection of Antibody to the 72– and 90–kilodalton Glycoproteins of Trypansoma cruzi," JID 155(3):561–564 (1987).

J.O. Previato, et al., "Primary Structure of the Oligosaccharide Chain of Lipopeptidophosphoglycan of Epimastigate Forms of Trypanosoma cruzi," J. Biol. Chem. 265(5):2518–2526 (1990).

C.T. Pan, "Cultivation of the Lesihmaniform Stage pf Trypanosoma cruzi in cell freemedia at Different Temperatures," Am. J. Trop. Med. and Hygiene 17(6):823–832 91968).

P.M. Rainey, et al., "Biochemical and Molecular Characterizationof Leishmania pifanoi amastigotes in Continuous Axenic Culture," Molec. and Biochem Parasit. 49:111–118 (1991).

S.C. Pan, "Establishment of Clone of Trypanosoma cruzi and Their Characterization in vitro and in vivo," Bull. of WHO 60(1):101–107 (1982).

A.A. Pan, et al., "Anastigote and Epimastigote State–Specific Components of Trypanosoma cruzi Characterized by Using Monoclonal Antibodies," J. Immunol. 143:1001–1008 (1989).

M.A. Winkler, et al., "Catalytic Site of Calmodulin–dependent Protein Phosphatase From Bovine Brain Residues in Subunit A," Proc. Natl. Acad. Sci. USA 81:3054–3058 (1984).

U.K. Laemmli, "Cleavage of Structural Proteins During the Assembly of the Head of Bacteriophase T4," Nature 227:680–685 (Aug. 15, 1970).

S. Bauminger, et al., "The Use ofCarbodiimides in the Preparation of Immunizing Conjugates", Methods in Enzyme 70:151–159 (1980).

W.M. Hunter, et al., "Preparation of Iodine–131 Labelled Human Growth Hormone of High Specific Activity," Nature 194:495–496 (May 5, 1962).

R.C.K. Wong, et al., "Immune Precipitation and Immunoblotting For The Dection of Trypanosoma cruzi Antigens," Trans. Royal Soc. Trop. Med. and Hygiene 80:275–281 (1986).

M. Gottlieb, "A Carbohydrate–Containing Antigen from Trypansoma cruzi and its Detection in the Circulation of Infected Mice," J. of Immunol. 119(2):465–470 (1977).

F. Zicker, et al., "Trends of T. cruzi Infection Based on Data From Blood Bank Screening," Rev. Inst. Med. Trop. Sao Paulo 32(2):132–137 (1990).

M.E. Camargo, et al., "Hemagglutination With Preserved, Sensitized Cells, a Practical Test For Routine Serologica Diagnosis of American Trypanosomaisis," Rev. Inst. Med. Top. Sao Paulo 15(2):81–85 (1973).

M.E. Camargo,e t al., "Cross–Rectivity in Fluorescence Tests for Trypanosoma and Leishmania Antibodies," Am. J. Trop. Med. and Hygiene 18(4):500–505 (1969).

M.Schechter,e t al., "Further Evaluation of Lectin Affinity Purified Glycoprotein (GP90) in the Enzyme Linked Immunoaborbant Assay (ELISA) for Diagnosis of Trypansoma Cruzi Infection," Trans. Royal soc. Trop. Med. and Hygiene 79:637–640 (1985).

G.A. Schmunis, et al., "Anti–Trypanosoma cruzi Agglutination in Acute Human Chagas' Disease," Am. J. Trop. Med. Hyg. 29:170–178 (1980).

I.G. Kagan, "American Trypanosomiasis (Chagas' Disease)" in V. Hanba, ed., Immunological Investigation of Trop. Par. Diseases pp. 49–64 91980).

Anonymous, "Mem. Insti. Oswaldo Cruz, Rio de Janeiro", Suppl. 81: 192–211 (Nov., 1986).

Campetella, O. et al. "The major cysteine proteinase (cruzipain) from Trypanosoma–cruzi is encoded by multiple polymorphic tandemly organized genes located on different chromosomes". Molecular and Biochemical Parasitology. vol. 50 (1992), pp. 225–234.

Cazzulo, Juan Jose et al. "Further characterization and partial amino acid sequence of a cysteine proteinase from Trypanosoma cruzi". Molecular and Biochemical Parasitology. vol. 33 (1989), p. 33–42.

Cooper, Robin et al. "Characterization of a candidate gene for GP72, an insect stage–specific antigen of Trypanosoma cruzi". Molecular and Biochemical Parasitology. vol. 49 (1991)), p. 45–60.

Hellman, Ulf et al. "Self–proteolysis of the cysteine proteinase, cruzipain, from Trypanosom cruzi gives a major fragment corrsponding to its carboxy–terminal domain". Molecular and Biochemical Parasitology. vol. 44 (1991), pp. 15–22.

Murta, Ana C.M. et al. "Structural and functional identification of GP57/51 antigen of Trypanosoma cruzi as a cysteine proteinase". Molecular and Biochemical Parasitology. vol. 43 (1990), pp. 27–38.

Mariinez, Javier et al. "Anomalous elecrophoretic behaviour of the major cysteine proteinas (cruzipain) from Trypanosoma cruzi in relation to its apparent molecular mass". FEMS Microbiology Letters. vol. 95 (1992), pp. 225–230.

"Pierce Immuno Technology Catalog & Handbook", vol. 1, published Jul. 1990 by Pierce (Rockford, IL), p. A–5.

Transfusion, vol. 31, No. 8 Supplement, issued 1991, Pan et al. "A Specific and Sensitive Enzyme Immunoassay and Confirmatory Test for the Detection of Antibody to Trypanosoma cruzi (Chagas' Disease)", Abstrct no. S43, published in Oct. 1991.

British Medical Bulletin, vol. 41, No. 2, issued apr. 1985, Snary, "Biochemistry of Surface Antigens of *Trypanosoma cruzi*", pp. 144–148.

European Journal of Biochemistry, vol. 182, No. 2, issued Jun. 15, 1989, De Arruda et al., "Terminal Beta–D–Galactofuranosyl Epitopes Recognized by Antibodies that Inhibit *Trypanosoma cruzi* Internalization into Mamalian Cells", pp. 413–421.

Molecular and Biochemical Parasitology, vol. 33, published by Elsevier in 1989, Harth et al., "Purification and Characterization of Stage–Specific Glycoproteins from *Trypanosoma cruzi*", pp. 143–150.

Intorduction to Protein Purification, 1989, Janson et al., VCH Publishers: New york, pp. 3, 281–283, and 311.

Parisitology, vol. 65, issued 1972, M. A. Miles, "Trypanosoma cruzi—Milk Transmission of Infection and Immunity from Mothers to Young", pp. 1–9.

Revista Da Sociedade Brasileira de medicina Tropical, vol. 20, No. 4, issued in 1987, A. Rocha et al., "O Teste Imunoenzimatico elisa no liquido pericardico: novometodo para o diagnostico post–mortem da doenca de chagas", (English summary p. 215) pp. 213–216.

Rev. Neurol. Arg. vol. 3, No. 3, issued in 1977, J. O. Marques et al., "Inmunopatologia del liquido cafaloraquideo", (English summary p. 450) pp. 448–451.

The Lancet, vol. 2 (8356), issued Oct. 22, 1983, Schechter et al., "Purified Trypanosoma Cruzi Specific Glycoprotein for Discriminative Serological Diagnosis of South American Trypanosomiasis (Chagas' Disease)", pp. 939–941.

Journal of Immunology, vol. 137, No. 4, issued Aug. 15, 1986, Scharfstein et al., "*Trypanosoma cruzi*: Characterization and Isolation of a 57/51,000 m.w. Surface Glycoprotein (GP57/51) Expressed by Epimastigotes and Bloodstream Trypomastigotes", pp. 1336–1341.

Biochemistry, vol. 22, No. 21, issued in 1983, Mendonca–Previato et al., "Chemical Structure and Antigenic Aspects of Complexes Obtained from Epimastigotes of *Trypanosoma cruzi*", pp. 4980–4987.

PPD Analytical Research, Carbohydrate Binding Properties of Snowdrop Lectin, pp. 729–734.

Eur. J. Biochem., vol. 192 issued in 1990, de Lederkremer et al., "Structural Features of th Lipopeptidophosphoglycan from *Trypanosoma cruzi* Common with the Glycophosphatidylinositol Anchors", pp. 337–345.

Biochimica et Biophysica Acta, vol. 444, issued in 1976, de Lederkremer et al., "A Lipopeptidophosphoglycan from *Trypanosoma cruzi* (Epimastigota)" pp. 85–96.

Biochimica et Biophysica Acta, vol. 842, issued in 1985, Ferguson et al., "Comarative Compositions of Cell Surface Glycoconjugates Isolated from *Trypanosoma cruzi* Epimastigotes", pp. 39–44.

Biochemistry International, vol. 10 No. 1, issued in 1985, De Lederkremer et al., "Trypanosoma Cruzi: Aminoacid and Phosphorus Linkages in the Lipopetidophosphoglycan", pp. 89–96.

ASSAY FOR CHAGAS' DISEASE AND REAGENTS FOR ITS USE

This is a division of U.S. patent application Ser. No. 08/275,086 filed Jul. 13, 1994, now U.S. Pat. No. 5,550,027, which is a continuation of U.S. patent application Ser. No. 07/911,590 filed Jul. 10, 1992, now abandoned.

BACKGROUND OF THE INVENTION

This invention relates generally to the detection of parenterally transmitted diseases and their detection, and more particularly, relates to *Trypanosoma cruzi* which is the causative agent of Chagas' Disease, and assays for its detection in test samples.

The protozoan parasite *Trypanosoma cruzi* is the causative agent responsible for a disease known as Chagas' Disease or as American Trypanosomiasis. The geographical range of this disease in the Americas is as far north as California and Maryland and as far south as regions in Argentina and Chile. It has been estimated that 90 million people are at risk, and that an additional 12 to 63 million individuals are infected with this parasite. See, for example, G. A. Schmunis, *Transfusion* 31:547–557 (1991); Anonymous, *WHO Technical Report Series* 1991 811:1–93 (1991); and S. Kingman, *New Scientist* 132:16–17 (1991). The first indigenous case of Chagas' Disease in North America was reported in 1955. N. C. Woody et al., *JAMA* 159:676–677 (1955); R. J. Schiffler et al., *JAMA* 251:2983–84 (1984); J. D. Pearlman, *Am. J. Med.* 75:1057–1060 (1983); T. R. Navin, *Am. J. Public Health* 75:366–369 (1985); and Anonymous, *Texas Health Bull.* 159:11–13 (1955).

Chagas' Disease is transmissable through blood products; the transmission of Chagas' Disease through blood transfusion in the United States has been recognized for some time. Two recent serological surveys in the Washington, D.C. area have indicated that several individuals residing in that area, originally from El Salvador and Nicaragua, had sera reactive for Chagas' Disease. L. V. Kirchhoff et al., *JAMA* 254:3058–3060 (1985); and L. V. Kirchhoff et al., *Am. J. Med.* 82:915–920 (1987). It has been estimated from this survey that there are up to 100,000 individuals living in the United States who are chronically infected with *T. cruzi*. A. Skolnick, *JAMA* 265:173 (1991). In a separate report, of 1027 consecutive blood donations in Los Angeles County during a three-month period which were screened by a complement fixation test for Chagas' Disease, there were ten initial reactives and one confirmed case. P. Kerndt et al., *Transfusion* 28:31S Abstract s108 (1988) and P. Kerndt et al., *Transfusion* 31:814–818 (1991). Imported Chagas' Disease has been recognized in Europe as well, with a documented case of congenital *T. cruzi* infection reported in Sweden. P. O. Pehrson et al, *Scand. J. Infect. Dis.* 13:307–308 (1981).

*Trypanosoma cruzi* has one of the most complex life cycles of trypanosomes found in man. Trypomastigotes circulate in the blood of vertebrate hosts and are transmitted by blood-sucking triatomid insects. The disease also can be spread by blood transfusion, through intravenous drug use, by congenital transmission, by sexual activity, by organ transplant or through breast milk. See, for example, A. Skolnick, *JAMA* 262:1433 (1989); P. Nickerson et al., *Ann. Intern. Med.* 111:851–853 (1989); Anonymous, *Clinica* 354:16 (1989); L. V. Kirchhoff, *Ann. Intern. Med.* 111:773–775 (1989); G. Bonfim et al., *ISBT/AABB Joint Congress*, Abstract S445, 112 (Nov. 10–15, 1990); P. Kerndt et al., *Transfusion* 28:S108 (1988); I. H. Grant et al., *Ann. Intern. Med.* 111:849–851 (1989); M. Boxaca et al., *Int Conf. AIDS* 6:437 (Abstract 3141) (1991); S. G. Sandler, *Am. Red Cross Blood Services Letters* 89:1–10 (1989); A. L. Bittencourt, *Am. J. Dis. Child* 130:97–103 (1976); R. Hoff et al., *Trans. R. Soc. Trop. Med. Hyg.* 72:247–250 (1978); M. D. Gudino et al., in *Emerging Global Patterns in Transfusion-Transmitted Infections*, R. G. Westphal et al., eds., Arlington, Va., American Association of Blood Banks, 65–86 (1990); I. G. Kagan et al., *Rev. Biol. Trop.* 14:55–73 (1966); I. C. P. Dias et al., *Mem. Inst. Oswaldo Cruz* 79:139–147 (1984); and J. H. Maguire et al., "American Trypanosomiasis" in *Infectious Diseases*, P. D. Hoepricke et al., eds, Philadelphia: J. P. Lippincott, pp. 1257–1266 (1989).

Diagnosis of the disease commonly is accomplished by identification of parasites in the blood, cerebrospinal fluid, fixed tissue or lymph node during periods of high fever; however, the organisms may be difficult to detect during the latent (or so-called indeterminant) phase, or during chronic stages of infection. In xenodiagnosis, the intestinal contents of insect vectors are examined for *T. cruzi* several weeks after these parasites feed on the blood of a suspected patient. However, this procedure is laborious and lacks sensitivity. E. L. Segura, "Xenodiagnosis" in *Chagas' Disease Vectors*, R. R. Brenner et al., eds., 11:41–45, Boca Raton, Fla., CRC Press (1987)

Several different serologic methodologies have been used to diagnose Chagas' Disease. These methodologies include indirect immunofluorescence, indirect hemagglutination, complement fixation and enzyme immunoassay. See, for example, F. Zicker et al., *Bull. World Health Organ.* 68:465–471 (1990); M. E. Carmargo, *Rev. Inst. Med. Trop. Sao Paulo* 8:227–234 (1977); M. E. Carmargo et al., *Bull. Pan Am. Health Organ* 19:233–264 (1985); A. A. Pan et al., *J. Infect. Dis.* (165:585–588 [1992]); A. A. Pan et al., *Am. J. Trop. Med. Hyg.* 45:120 Abstract 66 (1991); A. F. Ferreira et al., *Rev. Inst. Med. Trop. San Paulo* 33:123–128 (1991). Specific antibody responses to the parasite are detectable after infection, and the titers typically remain high for life. D. M. Israelski et al., *Am. J. Trop. Med. Hyg.* 39:445–455 (1988); R. Lelchuck et al., *Clin. Exp. Immunol.* 6:547–555 (1970); N. H. Vattuone et al., Am. J. Trop. Med. Hyg. 76:45–47 (1973).

The natural transmission of Chagas' Disease in humans occurs when skin or mucosa come in contact with feces of infected bugs. The signs and symptoms are so mild that the recent infection usually is not associated with *T. cruzi* infection. Even without treatment, the majority of individuals recover from the acute stages of disease. After a latent period of years or decades, a percentage of individuals (20–40%) develop the cardiac or gastrointestinal symptoms that characterize chronic Chagas' Disease. Persistence of parasitemia in asymptomatic individuals and survival of the parasite in banked blood and blood components increases the dangers of transmission of Chagas' Disease by blood transmision; infected blood used for transfusion in blood banks poses a significant public health problem. A rapid and reliable assay with standardized components for screening and confirming blood donors for Chagas' Disease thus would be extremely useful in preventing transfusion of the disease by blood banks.

SUMMARY OF THE INVENTION

The present invention provides a method which can be utilized as a confirmatory test for the presence of antibodies to *T. cruzi* in a test sample. The method comprises (a) determining the presence of a first *T. cruzi* antibody in a test sample, which comprises (i) contacting a first aliquot of a test sample with a first *T. cruzi* antigen attached to a solid support to form a mixture and incubating same to form first antigen/antibody complexes, (ii) contacting said first antigen/antibody complexes with an indicator reagent for a time and under conditions sufficient to form first antigen/antibody/indicator reagent complexes, and (iii) detecting the presence of the first *T. cruzi* antibody by measuring the signal generated; (b) determining the presence of a second *T. cruzi* antibody in a test sample, which comprises (i) contacting a second aliquot of a test sample with a second *T. cruzi* antigen attached to a solid support to form a mixture and incubating same to form second antigen/antibody complexes, (ii) contacting said second antigen/antibody complexes with an indicator reagent for a time and under conditions sufficient to form second antigen/antibody/indicator reagent complexes, and (iii) detecting the presence of the second *T. cruzi* antibody by measuring the signal generated; and (c) determining the presence of a third *T. cruzi* antibody in a test sample, which comprises (i) contacting a third aliquot of a test sample with a third *T. cruzi* antigen attached to a solid support to form a mixture and incubating same to form third antigen/antibody complexes, (ii) contacting said third antigen/antibody complexes with an indicator reagent for a time and under conditions sufficient to form third antigen/antibody/indicator reagent complexes and (iii) detecting the presence of the third *T. cruzi* antibody by measuring the signal generated. The presence of at least two specific antibodies confirms the presence of *T. cruzi* antibody in the test sample. *T. cruzi* antigens for use in the assay include Gp90, Gp 60/50 and LPPG. The antigens are used with the proviso that the antigen used as the first antigen is not used for the second antigen in step (b) or the third antigen in step (c), the antigen used as the second antigen is not used for the first antigen in step (a) or the third antigen in step (c), and the antigen used as the third antigen is not used for the first antigen in step (a) or the second antigen in step (b). The indicator reagent used in the assay comprises a label which is selected from the group consisting of a chromogen, a catalyst, a luminescent compound, a chemiluminescent compound, a radioactive element, and a direct visual label.

The present invention also provides diagnostic reagents for use in a method for detection of *T. cruzi* antibody. These reagents comprise Gp90, Gp 60/50 and LPPG. Also provided are diagnostic test kits for confirmatory tests which include Gp 90, Gp60/50 and LPPG.

In addition, processes for purifying the Gp60/50 and the LPPG antigens also are provided. The process for purifying the Gp60/50 antigen of *T. cruzi*, comprises (a) isolating the membrane of the epimastigote stage of *T. cruzi* by dounce homogenization; (b) extracting the Gp60/50 antigen; (c) applying the resultant extract of step (b) to a *Galanthus nivalis* lectin affinity column and eluting with a carbohydrate; and (d) purifying the eluate with an affinity column comprising a monoclonal antibody specific for Gp60/50. The extraction step preferably is performed with a non-ionic detergent.

Further, the present invention provides a process for linking an antigenic glycolipid of *T. cruzi* to a protein carrier, which comprises (a) obtaining the glycolipid lipophosphonopeptidoglycan (LPPG) from the epimastogote stage of *T. cruzi*; (b) linking LPPG of step (a) with a protein using ethyldimethyl-amino-propyl-carbodiimide (EDAC) by (i) contacting LPPG with EDAC to form a resultant mixture and incubating said mixture for a time and under conditions sufficient to activate the mixture, (ii) incubating the activated mixture with the protein for a time and under conditions sufficient to link the LPPG with the protein; (c) purifying the mixture; and (d) eluting the LPPG from the mixture. The protein preferred to be linked is bovine serum albumin (BSA). Further, it is preferred that the purification of step (c) is performed by passing the mixture over blue dextran Sepharose.

BRIEF DESCRIPTION OF THE DRAWINGS

FIG. 2A is a graph of sample C, obtained from San Antonio, Tex.;

FIG. 2B is a graph of sample b, obtained from Los Angeles, Calif.;

FIG. 2C is a graph of a sample from Brazil;

FIG. D is a Chagas' Disease EIA Latin American Positive Control (Abbott Laboratories, Abbott Park, Ill.).

Figure 3:
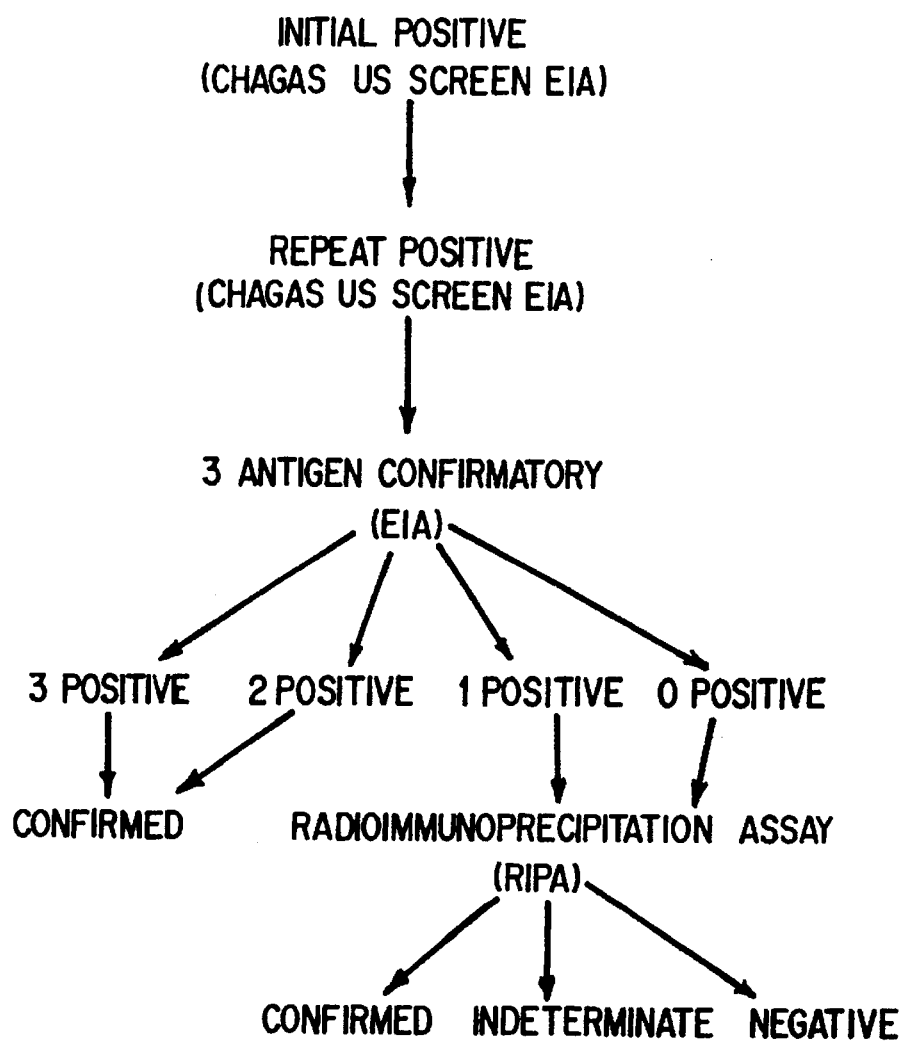

FIG. 3 is a scheme for confirmation of seropositivity for *T. cruzi*.

DETAILED DESCRIPTION OF THE INVENTION

An assay for the detection of *T. cruzi* antibody analyte in a test sample is provided. The assay preferably is performed as an immunoassay, although the present invention is not limited to immunoreactive assays. Any assay utilizing specific binding members can be performed. A "specific binding member," as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding member, for example, an analyte-analog. Immunoreactive specific binding members include antigens, antigen fragments; antibodies and antibody fragments, both monoclonal and polyclonal; and complexes thereof, including those formed by recombinant DNA methods.

"Analyte," as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. "Analyte" also includes any antigenic substances, haptens, antibodies, and combinations thereof. As a member of a specific binding pair, the analyte can be detected by means of naturally occurring specific binding partners (pairs) such as the use of intrinsic factor protein in the capture and/or indicator reagents for the determination of vitamin $B_{12}$, or the use of a lectin in the capture and/or indicator reagents for the determination of a carbohydrate. The analyte can include a protein, a peptide, an amino acid, a hormone, a steroid, a vitamin, a drug including those administered for therapeutic purposes as well as those administered for illicit purposes, a bacterium, a virus, and metabolites of or antibodies to any of the above substances.

The test sample can be a mammalian biological fluid such as whole blood or whole blood components including red blood cells, white blood cells including lymphocyte or lymphocyte subset preparations, platelets, serum and plasma; ascites; saliva; stools; cerebrospinal fluid; urine; sputum; trachael aspirates and other constituents of the body which may contain or be suspected of containing the analyte (s) of interest. The test sample also can be a culture fluid supernatant, or a suspension of cultured cells. Mammals or others whose body fluids can be assayed for *T. cruzi* antibody analyte according to the present invention include humans and primates, as well as other mammals who are suspected of containing these analytes of interest.

The indicator reagent comprises a label conjugated to a specific binding member of each analyte. Each indicator reagent produces a detectable signal at a level relative to the amount of the analyte, if any, present in the test sample. In a preferred embodiment, each indicator reagent, while comprising a specific binding member of a different analyte, is conjugated to the same signal generating compound (label), which is capable of generating a detectable signal. In general, the indicator reagent is detected or measured after it is captured on the solid phase material. In the present invention, the total signal generated by the indicator reagent (s) indicates the presence of one or more of the analytes in the test sample. It is contemplated that different signal generating compounds can be utilized in the practice of the present invention. Thus, for example, different fluorescent compounds could be utilized as the signal generating compounds, one for each indicator reagent, and detection could be determined by reading at different wavelengths. Or, a short-lived chemiluminescent compound such as an acridinium or phenanthridium compound and a long-lived chemiluminescent compound such as a dioxetane can be utilized to generate signals at different times for different analytes. Methods which detail the use of two or more chemiluminescent compounds which are capable of generating signals at different times are the subject matter of co-pending patent application U.S. Ser. No. 636,038, which enjoys common ownership and is incorporated herein by reference. Acridinium and phenanthridinium compounds are described in co-pending U.S. patent application Ser. No. 07/271,763 filed Jun. 23, 1989, which enjoys common ownership and is incorporated herein by reference.

In addition to being either an antigen or an antibody member of a specific binding pair, the specific binding member of the indicator reagent can be a member of any specific binding pair, including either biotin or avidin, a carbohydrate or a lectin, a complementary nucleotide sequence, an effector or a receptor molecule, an enzyme cofactor or an enzyme, an enzyme inhibitor or an enzyme, and the like. An immunoreactive specific binding member can be an antibody, an antigen, or an antibody/antigen complex that is capable of binding either to the analyte as in a sandwich assay, to the capture reagent as in a competitive assay, or to the ancillary specific binding member as in an indirect assay. If an antibody is used, it can be a monoclonal antibody, a polyclonal antibody, an antibody fragment, a recombinant antibody, a mixture thereof, or a mixture of an antibody and other specific binding members. The details of the preparation of such antibodies and their suitability for use as specific binding members are well known to those in the art.

The signal generating compound (label) of the indicator reagent is capable of generating a measurable signal detectable by external means. The various signal generating compounds (labels) contemplated include chromagens; catalysts such as enzymes for example, horseradish peroxidase, alkaline phosptasae, and B-galactosidase; luminescent compounds such as fluorescein and rhodamine; chemiluminescent compounds such as acridinium compounds, phenanthridinium compounds and dioxetane compounds; radioactive elements; and direct visual labels. The selection of a particular label is not critical, but it will be capable of producing a signal either by itself or in conjunction with one or more additional substances. A variety of different indicator reagents can be formed by varying either the label or the specific binding member.

The capture reagents of the present invention comprise a specific binding member for each of the analytes of interest which are attached to at least one solid phase and which are unlabeled. Although the capture reagent is specific for the analyte as in a sandwich assay, it can be specific for an indicator reagent or analyte in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample. This attachment can be achieved, for example, by coating the specific binding member onto the solid phases by absorption or covalent coupling. Coating methods, and other known means of attachment, are known to those in the art.

The specific binding member of the capture reagent can be any molecule capable of specifically binding with another molecule. The specific binding member of the capture reagent can be an immunoreactive compound such as an antibody, antigen, or antibody/antigen complex. If an antibody is used, it can be a monoclonal antibody, a polyclonal antibody, an antibody fragment, a recombinant antibody, a mixture thereof, or a mixture of an antibody and other specific binding members.

The "solid phase" is not critical and can be selected by one skilled in the art. Thus, latex particles, microparticles, magnetic or non-magnetic beads, membranes, plastic tubes, walls of wells of reaction trays, glass or silicon chips and tanned sheep red blood cells are all suitable examples. Suitable methods for immobilizing capture reagents on solid phases include ionic, hydrophobic, covalent interactions and the like.

A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, and other configurations known to those of ordinary skill in the art.

It is contemplated and within the scope of the invention that the solid phase also can comprise any suitable porous material with sufficient porosity to allow access by detection antibodies and a suitable surface affinity to bind antigens. Microporous structures are generally preferred, but materials with gel structure in the hydrated state may be used as well. Such useful solid supports include:

natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-exisitng natural polymer. All of these materials may be used in suitable shapes, such as films, sheets, or plates, or they may be coated onto or bonded or laminated to appropriate inert carriers, such as paper, glass, plastic films, or fabrics.

The porous structure of nitrocellulose has excellent absorption and adsorption qualities for a wide variety of reagents including monoclonal antibodies. Nylon also possesses similar characteristics and also is suitable.

It is contemplated that such porous solid supports described hereinabove are preferably in the form of sheets of thickness from about 0.01 to 0.5 mm, preferably about 0.1 mm. The pore size may vary within wide limits, and is preferably from about 0.025 to 15 microns, especially from about 0.15 to 15 microns. The surfaces of such supports may be activated by chemical processes which cause covalent linkage bf the antigen or antibody to the support. The irreversible binding of the antigen or antibody is obtained, however, in general, by adsorption on the porous material by poorly understood hydrophobic forces.

Preferred solid phase materials for flow-through assay devices include filter paper such as a porous fiberglass material or other fiber matrix materials. The thickness of such material is not critical and will be a matter of choice, largely based upon the properties of the sample or analyte being assayed, such as the fluidity of the test sample.

To change or enhance the intrinsic charge of the solid phase, a charged substance can be coated directly to the material or onto microparticles which then are retained by a solid phase support material. Alternatively, microparticles can serve as the solid phase, by being retained in a column or being suspended in the mixture of soluble reagents and test sample, or the particles themselves can be retained and immobilized by a solid phase support material. By "retained and immobilized" is meant that the particles on or in the support material are not capable of substantial movement to positions elsewhere within the support material. The particles can be selected by one skilled in the art from any suitable type of particulate material and include those composed of polystyrene, polymethylacrylate, polypropylene, latex, polytetrafluoroethylene, polyacrylonitrile, polycarbonate, or similar materials. The size of the particles is not critical, although it is preferred that the average diameter of the particles be smaller than the average pore size of the support material being used. Thus, embodiments which utilize various other solid phases also are contemplated and are within the scope of this invention. For example, ion capture procedures for immobilizing an immobilizable reaction complex with a negatively charged polymer, described in co-pending U.S. patent application Ser. No. 150,278 corresponding to EP Publication No. 0326100, and U.S. patent application Ser. No. 375,029 (EP Publication No. 0406473), which enjoy common ownership and are incorporated herein by reference, can be employed according to the present invention to effect a fast solution-phase immunochemical reaction. An immobilizable immune complex is separated from the rest of the reaction mixture by ionic interactions between the negatively charged polyanion/immune complex and the previously treated, positively charged porous matrix and detected by using various signal generating systems previously described, including those described in chemiluminescent signal measurements as described in co-pending U.S. patent application Ser. No. 921,979 corresponding to EPO Publication No. 0 273,115, which enjoys common ownership and which is incorporated herein by reference.

Also, the methods of the present invention can be adapted for use in systems which utilize microparticle technology including automated and semi-automated systems wherein the solid phase comprises a microparticle. Such systems include those described in pending U.S. patent application Ser. No. 425,651 and U.S. Pat. No. 5,089,424, which correspond to published EPO applications Nos. EP 0 425 633 and EP 0 424 634, respectively, and U.S. Pat. No. 5,006,309 all of which enjoy common ownership and are incorporated herein by reference. Such systems also include U.S. patent application Ser. No. 07/859,218 filed Mar. 27, 1992, which enjoys common ownership and is incorporated herein by reference.

One aspect of the invention is a confirmatory assay for antibody to *T. cruzi*, the agent of Chagas' Disease. This assay involves coating a first solid phase with a first *T. cruzi* antigen, coating a second solid phase with a second *T. cruzi* antigen, and coating a third solid phase with a third *T. cruzi* antigen. An aliquot of a test sample, previously screened for *T. cruzi* antibody and repeat reactive in a screening test, is placed in contact with each solid phase. Thus, an aliquot of a test sample is separately placed in contact with each solid phase and reacted separately. The *T. cruzi* antigen(s) preferred for use in this confirmatory assay are Gp90, Gp 60/50 and LPPG-BSA. The resultant mixture is incubated for a time and under conditions sufficient to form antigen-antibody complexes. Then, an indicator reagent specific for each antibody and attached to a label capable of generating a measurable signal is contacted with the antigen-antibody complexes and incubated for a time and under conditions sufficient to form antigen/antibody/indicator reagent. The signal generated from each solid phase is determined. The presence of *T. cruzi* is determined as a function of the signal generated from the solid phase-indicator reagent. The presence of antibody to at least two of the three *T. cruzi* antigens indicates the confirmed presence of *T. cruzi* antibody in the test sample.

In a second aspect of the present invention, at least one antigen of the three antigens disclosed above is coated on a solid support. A test sample is contacted with the solid phase and the resultant mixture is incubated for a time and under conditions sufficient to form antigen/antibody complexes. Then, an indicator reagent, which specifically reacts with the specific binding member(s) now attached to the solid support and is capable of generating a measurable signal, is added to the complexes, and the resultant second mixture is incubated for a time and under conditions sufficient to form antigen/antibody/indicator reagent. The signal generated from the solid phase/indicator reagent is measured; a signal generated which is greater than a pre-determined known negative control cut-off value is considered reactive, and thus, indicative of the presence of antibody to *T. cruzi*.

The eukaryotic organism *T. cruzi* has greater than 30,000 proteins; there is conversation of epitopes between members of the family of Trypanosomidae/Kinetoplastida. D. E. Lanar et al., *Mol. Biochem. Parasitol.* 3:327–341 (1981) and S. P. Craig et al., *Comp. Biochem. Physiol.* 95B:667–662 (1990). Further diversity of *T.cruzi* includes zymodemes or strain variability from one geographic location to the next. Xenodiagnosis must be performed with care to rule out chance of cross-reaction with *T. rangeli*, a parasite which has similar insect vectors but different locations of metacyclic trypomastigotes. The antigens used for the above described assay formats are purified to homogeneity from either the amastigote or epimastigote stages of *T. cruzi* and subsequently attached (coated) onto a solid support. The Gp90 and LPPG antigens previously have been characterized and the Gp90 antigen (s) has been shown to be immunogenic. See, for example, M. Schechter et al., *Lancet* 2:939–941 (1983); L. V. Kirchhoff et al., *J. Inf. Dis.* 155:561–564 (1987) and J. O. Previato et al., *J. Biol. Chem.* 265:2518–2526 (1990). However, the use of the combination of the three preferred *T. cruzi* antigens has not been described heretofore for use in a confirmatory or screening assay for antibody to *T. cruzi*. In the confirmatory assay, if the absorbance of a suspected sample is above the cutoff value in three-of-three or two-of-three determinations using *T. cruzi* antigens, it is considered as a confirmed positive sample for the disease. However, if the absorbance is not above the cutoff in any or in only one of three antigens utilized, the test sample is subjected to radioimmunoprecipitation RIPA. In RIPA, diagnostic bands exhibit characteristic banding patterns at 32, 34 and 90 kD. The titer of a positive test sample is reflected in 19 and 25 kD banding pattern. Thus, the test sample can fall into three categories: confirmed reactive, indeterminate reactive or negative.

The present invention will now be described by way of examples, which are meant to illustrate, but not to limit, the spirit and scope of the present invention.

EXAMPLES

Example 1

Culture of Parasites

Stock cultures of *T. cruzi* epimastigotes (available from the American Type Culture Collection, Rockville, Md.) were maintained in modified NNN medium (disclosed in C. Pan, *Am. J. Trop. Med. Hyg.* 17:823–832) 1968) with an overlay of UM-55 medium (as disclosed in P. M. Rainey et al., *Mol. Biochem. Parasitol.* 49:111–118 (1991); A. Pan, *Exp. Parasitol.* 58:72–80 (1984) at 24° C. following the procedures described in S. C. Pan, *Bull. World Health Organ.* 60:101–107 (1982); P. M. Rainey et al., *Mol. Biochem. Parasitol.* 41:111–118 (1991); and A. A. Pan et al., *J. Immunol,* 143:1001–1008 (1989). For experiments, epimastigotes were inoculated into 5 ml of UM-55 medium and passaged once. Five milliliters of this culture in mid-log phase of growth was used to inoculate a spinner flask containing 6 liters (1) of UM-55 medium and then was incubated for seven to ten days at 26° C.

Example 2

Production of *T. cruzi* Membranes

Epimastigotes or amastigotes of *T. cruzi* were grown to log phase, harvested and washed three times with phosphate buffered saline (PBS) (pH 7.4) by centrifugation at 6000×g. The final pellet of cells was resuspended in lysis buffer (consisting of 20 mM Tris-HCl [pH 7.3], 40 mM NaCl, 10 mM EDTA, 2 mM phenylmethyl sulfonyl fluoride ([PMSF] and 1 mM iodoacetamide). The organisms (50 ml packed epimastigotes or 20 ml packed amastigotes) were disrupted either by nitrogen cavitation (1500 psi for 15 minutes on ice) or by dounce homogenization. The lysates were subfractioned by differential centrifugation at 48,600×g for 30 minutes at 4° C., following the method described by A. A. Pan et al., supra.

Example 3

Preparation of *T. cruzi* Antigens for Assay Use

Gp 60/50. The Gp 60/50 glycoprotein of *T. cruzi* was purified from epimastigotes as follows. Briefly, the membrane-enriched pellet was solubilized for two hours at 4° C. in Buffer A (consisting of 20 mM Tris-HCl, [pH 7.2]) containing 150 mM NaCl, 2.0 mM iodoacetamide, 1 mM EDTA, 0.5 mM PMSF, 77 μM Aprotonin and two percent (2%) NP-40, and cleared by centrifugation at 48,000×g for 30 minutes at 4° C. The resultant supernatant fluid was applied to a 20 ml *Ganantbus nivulus* (GNA) lectin column (available from E. Y. Laboratories, San Mateo, Calif.), equilibrated in Buffer A which contained 0.5M NaCl, 0.1% NP-40 and 1 mM EDTA. The column was eluted with 0.3M alpha-methyl pyranoside in the same buffer. This eluate was applied to a monoclonal anti-Gp 60/50 (A. A. Pan et al., supra) IgG Sepharose column in phosphate-buffered saline (PBS, pH 7.2), washed with PBS, and eluted with 50 mM diethylamine as described in M. A. Winkler et al., *Proc. Natl. Acad. Sci.* 81:3054–3058 (1984). The antigen was analyzed by ten percent (10%) SDS-polyacrylamide gel electrophoresis (SDS-PAGE) under reducing conditions (U.

K. Laemmli, *Nature* 227:680–685 [1970]) and subjected to silver-staining (available from Bio-Rad, Richmond, Calif.), as described in M. A. Winkler et al., supra. This novel process produced a homogeneous glycoprotein (at least 20% carbohydrate). The *Gananthus nivulus* column isolated the glycoprotein in 1–2% yield from the majority of membrane-extracted proteins.

Gp 90. The Gp 90 kD antigen was isolated from axenically grown amastigote membranes using a similar technique as for GP 60/50, with the following modifications. A lentil lectin Sepharose 4B column (available from Pharmacia-LKB, Piscataway, N.J.) was substituted for the GNA lectin column, and the Buffer A used in the application, washing, and elution of the column contained 50 mM Tris-HCl (pH 7.5), 0.5 mM $CaCl_2$, 0.5 mM $MnCl_2$, 0.5M NaCl and 0.1% NP-40. The eluted material was affinity purified by a monoclonal anti-Gp 90 kD IgG2b(A. A. Pan et al., supra) Sepharose 4B column as described above. Protein concentration was measured for the membranes and purified antigens by the Pierce Coomassie Blue G-250 dye binding assay (available from Pierce, Rockford, Ill.). This antigen also was analyzed by SDS-PAGE, but stained by Coomassie Brilliant Blue R-250. The novel process produced a homogeneous glycoprotein for use in capturing and detecting *T. cruzi* antibodies. It was determined that about 24 ng gave a high signal in assays. Also, the yield of glycoprotein was at least 300 µg per 18 l of Amastigotes.

Example 4

Preparation of Lipophosphonopeptidoglycan (LPPG) Antigen for Assay Use

LLPG was isolated from the whole epimastigotes by the procedure of J. O. Previato et al., *J. Biol. Chem.* 265:2518–2526 (1990). Briefly, epimastigotes were thawed, washed three times in water, and extracted with 45 percent phenol in water. The aqueous phase was lyopkilized, applied to a P-100 gel filtration column in water, and the excluded peak lyophilized. The powder was extracted with chloroform:methanol:water (10:3:1), dried, then dissolved in water and precipitated with five (5) volumes of methanol at –20° C. LPPG was quantitated by orcinal-surfuric add assay for carbohydrates, following the method of C. A. White et al., "Oligosaccharides" in *Carbohydrate analysis. A Practical Approach*, M. F. Chaplin et al., eds. Washington D.C.: IRL Press, pp. 37–54 (1987). This glycolipid coated poorly onto the solid supports used (polystyrene beads) and therefore, a process was developed for linking the LPPG antigenic glycolipid from *T. cruzi* to a protein carrier so that the conjugate could be purified by affinity chromatography on blue dextran and subsequently coated onto solid phases for diagnostic assay use. LPPG was linked to bovine serum albumin (BSA) with ethyl diaminoprepylcarbodiimide (EDAC, available from Sigma Chem. Co., St. Louis, Mo.), following the methods disclosed in S. Bauminger et al., *Methods Enzymol.* 70:151–159 (1980) and modified as follows. LPPG was linked to bovine serum albumin (BSA) with EDAC in a two-step procedure, using a 1:2 mass ratio of LPPG to BSA. In the first step, LFPG was reacted at room temperature with EDAC, and then the activated mixture was reacted overnight with BSA. This material was purified by applying the mixture to a Blue dextran Sepharose (available from Sigma Chem. Co., St. Louis, Mo.) affinity column (10×1 cm), washing in PBS and eluting the LPPG-BSA conjugate with: 0.5M potassium thiocyanate. Titration of antigen coating (100 ng to 20 µg per bead) showed that 30 ng per ¼" bead was preferred. The resultant eluate can be diluted and directly coated onto beads.

Example 5

Three Bead Confirmatory Enzyme Immunoassay
Bead Coating Procedure

Each of the above antigens were separately coated onto polystyrene beads (0.625 cm in size), as follows: Polystyrene beads (2000 beads, 0.635 cm, available from Abbott Laboratories, Abbott Park, Ill.) were washed with isopropanol-water (71:400) for 20 minutes at 22° C. The fluid was removed by aspiration. 400 ml of PBS containing antigen (either 60 µg of LPPG-BSA prepared as in Example 4 or 60 µg of Gp60/50 prepared as in Example 3, or 48 µg of Gp90 prepared as in Example 3) was added to the beads. The beads and antigens were contacted with agitation for 2 hours at 40° C. Following agitation, the fluid was removed, and 400 ml of a blocking solution (3% bovine serum albumin in PBS) was added. The resultant mixture was agitated for 1 hour at 40° C. Then the fluid was removed, and 400 ml of an over-coat solution (5% sucrose and 0.5% gelatin in water) was added, the resultant mixture was incubated with agitation for 20 minutes at 22° C. The fluid was drained, and the beads were dried at 22° C. with nitrogen gas. The coated beads were stored dessicated at 4° C.

Immunoassay

Enzyme Immunoassay was performed as follows. 5 µl of a serum sample was diluted with 200 µl of specimen diluent in three separate reaction wells of a tray, and then incubated with each of three antigen coated beads (prepared as described hereinabove) for one (1) hour at 40° C. The beads then were washed with distilled water (Abbott Quikwash®, available from Abbott Laboratories, Abbott Park, Ill.), and incubated with conjugate (goat anti-human IgG [heavy and light chain] conjugated to horseradish peroxidase [available from Kierkegaard & Perry, Gaithersburg, Md.]) for thirty (30) minutes at 40° C. The beads then were washed, transferred to tubes and incubated with 300 µl of OPD tablet (Abbott Laboratories, Abbott Park, Ill.) dissolved in OPD diluent (comprising 50 mM citrate-phosphate containing 0.02% $H_2O_2$) for thirty (30) minutes at room temperature. The reaction was stopped by adding 1 ml of 1N $H_2SO_4$, and the absorbance was analyzed using an Abbott Quantum® spectrophotometer at 492 nm. In all experiments, a negative control (recalcified human plasma) and a positive control (inactivated human plasma, positive for antibody to *T. cruzi*) were included and assayed in triplicate. The cutoff value was determined from inspection of the sample absorbances in a negative population (SE Wisconsin; N=289). The cutoff value (S/N) was 3.3 for LPPG; 3.5 for Gp60/50; and 3.5 for Gp 90. The presence or absence of antibody to *T. cruzi* in an unknown sample was determined by relating the S/N to the cutoff value.

Example 6

Radioimmunoprecipitation (RIPA)

The epimastigote membrane enriched fraction obtained from Gp 60/50 purification was solubilized in 10 mM Tris-HCl (pH 7.8), 150 mM NaCl, 1 mM EDTA, 1 mM PMSF, 1 mM iodoacetamide, and 2.0% NP-40. The resultant mixture was equilibrated for one hour at 4° C., and the particulate material was separated from the soluble membrane protein by centrifugation at 20,000×g for thirty (30) minutes at 4° C. The resultant material was radiolabeled with Na $^{125}$I by chloramine-T method as described by W. M. Hunter et al., *Nature* 194:495–496 (1962). The labeled antigen was pre-absorbed with normal human serum-coated protein A Sepharose Cl-4B for one (1) hour at 4° C., and then it was centrifuged at 1000×g for ten (10) minutes. The unbound material (at $10^7$ cpm in a total volume of 20 to 25 μl) was incubated with 10 μl of the test serum overnight on ice. A 50 μl aliquot of 50% protein-A Sepharose CL-4B (Sigma Chemical Co., St. Louis, Mo.) suspension in PBS was added to the mixture and vortexed for 30 minutes at 4° C. The sample then was washed three (3) times in PBS containing 1% NP-40 and once in PBS containing 1% NP-40 and 0.05% sodium dodecyl sulfate (SDS). The sample was boiled for 5 minutes in SDS-loading buffer (2.3% SDS, 10% glycerol, 62.5 mM Tris-HCl, pH 6.8), centrifuged (12,500×g for 5 minutes) then the supernatant fluid was removed for analysis. The SDS-polyacrylamide-gel-electrophoresis was carried out according to the procedure of Laemmli (Nature 227:680–685 [1970]) in a 12.5% polyacrylamide gel. Autoradiography was conducted for 7–10 days at –70° C. with X-ray film (Kodak XAR-5) and Lightnight Plus intensifying screen (E. I. DuPont de Nemours & Co., Wilmington, Del.).

Example 7

Comparative Testing

Samples

Xenodiagnosis-positive samples were obtained from Institute Fatala Chaben, Buenos Aires, Argentina. Malaria sera were obtained from Africa (the Gambia) and India (Madras, India). African leishmaniasis sera were obtained from Sudan; schistosomiasis sera were obtained from Brazil. Negative samples, obtained from a "low risk" area of the United States (Milwaukee, Wis.), systemic lupus erythematosus (SLE) (Milwaukee, Wis.) and syphilis sera (Detroit, Mich.) also were assayed with the confirmatory assay of the invention.

Dilution Panel of Positive Serum

Several sera positive for antibody to T. cruzi, as determined by the confirmatory assay of the invention set forth in Example 5, were diluted appropriately to produce a dilution panel for determination of sensitivity. The positive control (human plasma heat inactivated at 56° C.) was diluted into normal human plasma to give an absorbance at 492 nm of 0.500 to 1.999, and was further diluted to 1:22 and 1:100. Several other positive samples were similarly diluted to 1:4 (high positive); 1:6 (medium positive); 1:9 (borderline positive); 1:13.5 (low positive); and 1:22 (non-reactive positive). Positive and negative controls also were tested (Abbott Laboratories, Abbott Park, Ill.). All sera were analyzed by the confirmatory assay of the invention and RIPA as described above.

Evaluation

A study was performed to evaluate the confirmatory assay of the invention and R/PA. Samples previously tested with a screening assay (Chagas Antibody EIA for Chagas' Disease, Abbott Laboratories, Abbott Park, Ill.) were used in the evaluation. These samples were obtained from eight field sites selected from the southwestern United States; the samples were unlinked except for classification at each specific location into Hispanic or non-Hispanic surname groups. Specimens were identified only by number for testing, the assays were performed, and the assay results were decoded at a later date. Total number of samples screened was 13,109. These samples were obtained from the following sites (Hispanic/non-Hispanic): Alburquerque, NM (224/224); Houston, Tex. (986/1326); McAllen, Tex. (664/259); San Antonio, Tex. (2396/1599); Los Angeles, Calif. (1050/1050); Sacramento, Calif. (1899/600); and San Diego (416/416). Samples were S/N greater than 3.0 (N=112) using the screening assay described above and were evaluated by the confirmatory assay of the invention by following the procedure detailed in Example 5 and RIPA according to the procedure of Example 6.

Results

1. Accuracy. The ability of the confirmatory assay of the invention to detect antibody to T. cruzi was established by comparison to consensus positive samples (samples in which there were positive results by both hemagglutination and indirect immunofluorescent antibody assays for Chagas' Disease). The assay of the invention was utilized on these 82 consensus positive samples. Fifty-six (56) samples demonstrated an absorbance value above the cutoff in three of three beads (sensitivity of 68.3% [24/82]). Twenty-four (24) samples were above the cutoff in only two of three antigens (29.3%) Two samples were positive on only one of three antigens; these had to be confirmed by RIPA. As seen in Table 1, the overall performance of the three-bead confirmatory assay was 97.56% (80/82) on consensus positive samples.

TABLE 1

| Sample Type | Sample Number | Assay of the Invention- Positive | Assay of the Invention- Negative | Sensitivity (%)* |
|---|---|---|---|---|
| Xenodiagnosed Positive | 28 | 28 | 0 | 100 |
| Consensus Positive** | 82 | 80 | 2 | 97.56 |
| Lesihmaniasis | 7 | 0 | 7 | |
| Malaria | 6 | 0 | 6 | |
| Toxoplasmosis | 6 | 0 | 6 | |
| Schistosomiasis | 10 | 0 | 10 | |
| Leprosy | 1 | 0 | 1 | |
| Syphilis | 2 | 0 | 2 | |
| Systemic lupus | 5 | 0 | 5 | |
| High Rheumatoid Factor | 2 | 0 | 2 | |

Figure 1A:
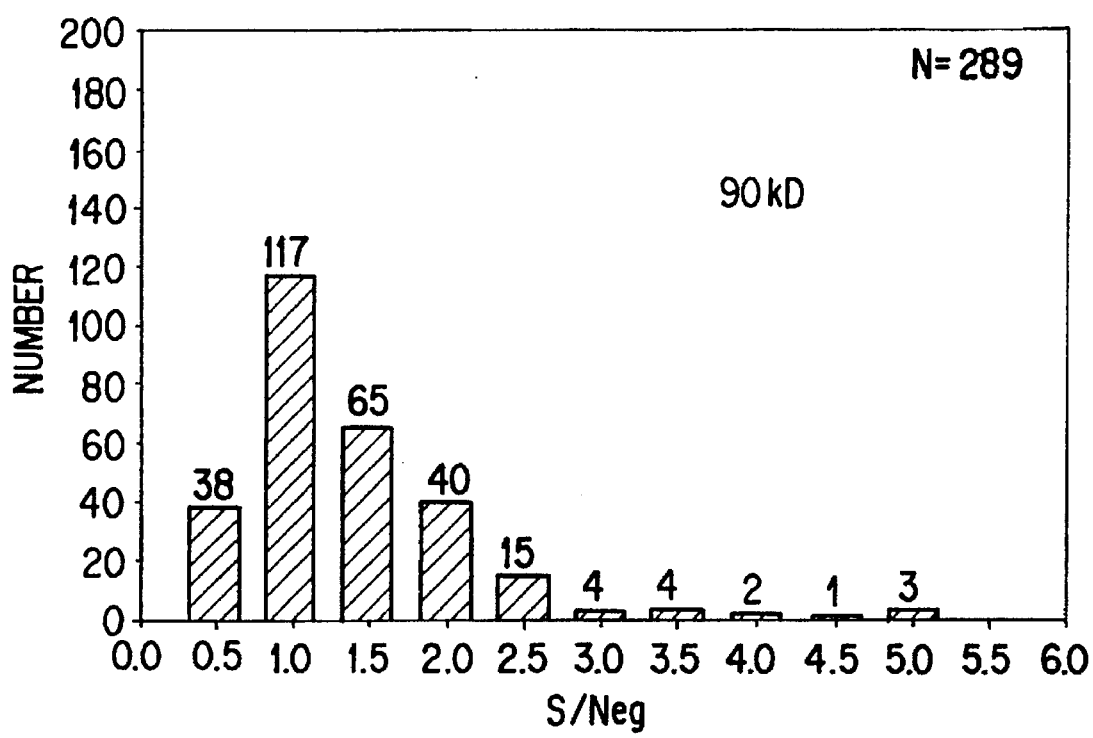
FIG. 1A is a bar graph wherein the number of sera from a negative population reactive with *T. cruzi*. Gp90 (90 kD) is shown along the vertical axis while the Signal to Negative ratio (S/Neg) is shown along the horizontal axis of the graph, wherein the number of sera tested was 289.
Figure 1B:
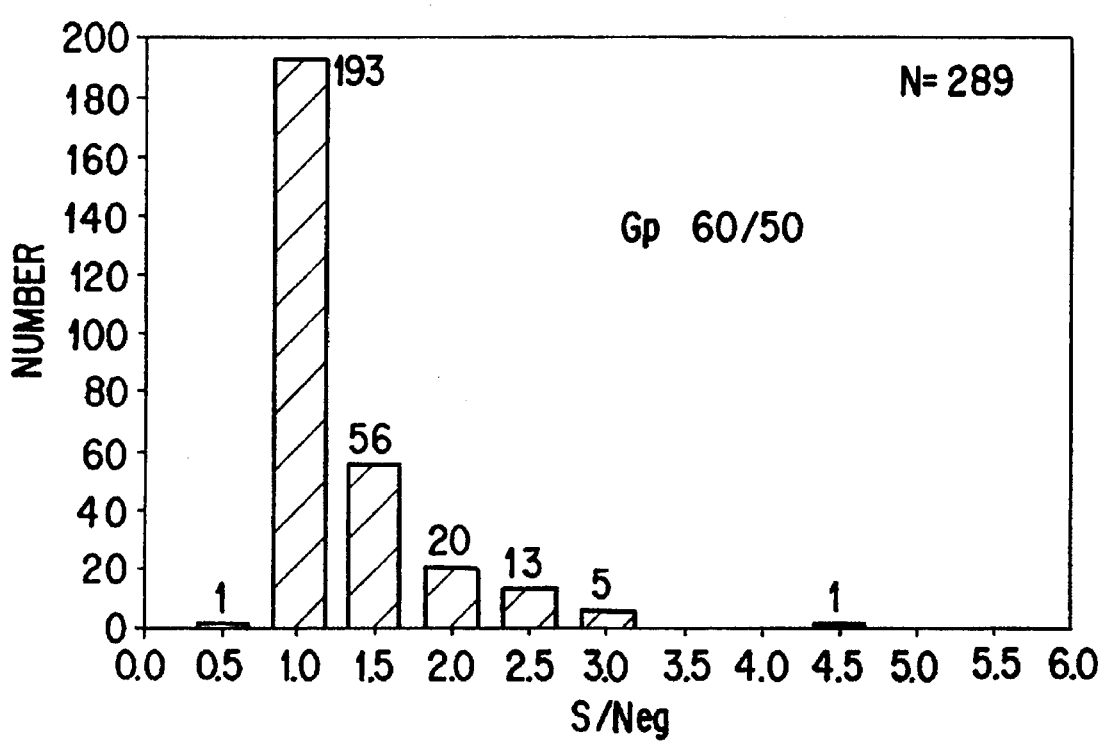
FIG. 1B is a bar graph wherein the number of sera from a negative population reactive with *T. cruzi* Gp60/50 is shown along the vertical axis while the Signal to Negative ratio (S/Neg) is shown along the horizontal axis of the graph, wherein the number of sera tested was 289.
Figure 1C:
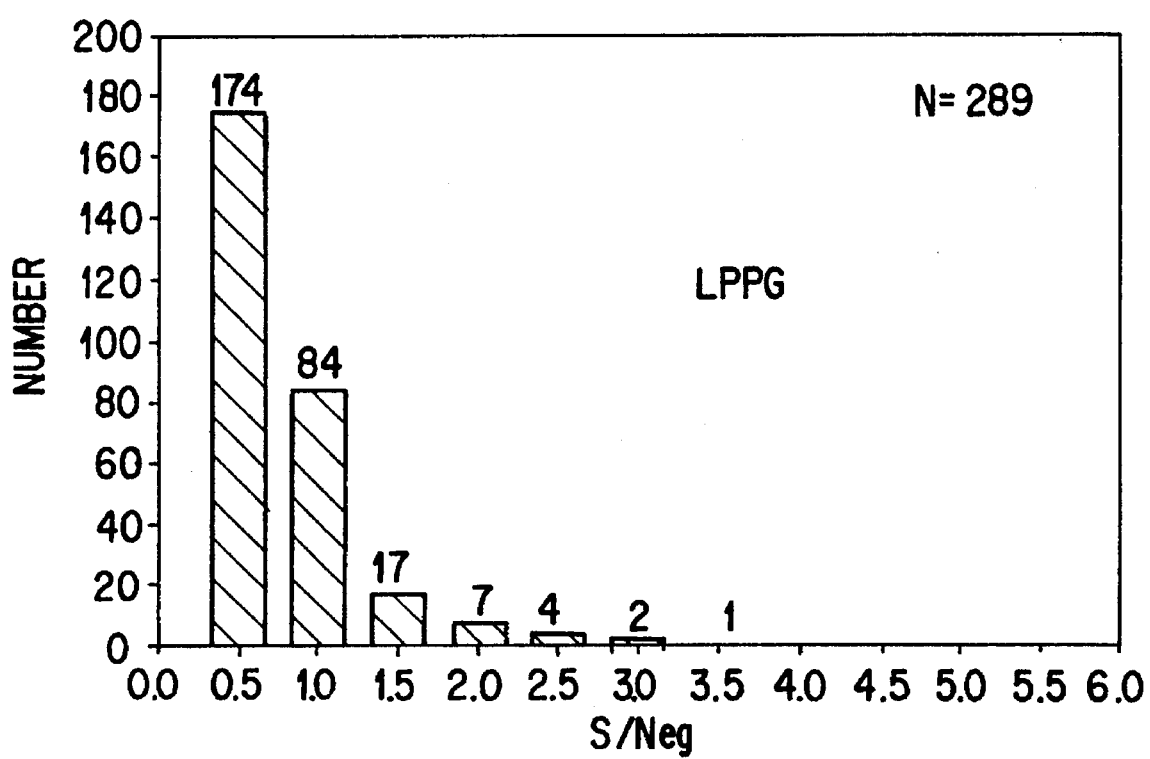
FIG. 1C is a bar graph wherein the number of sera from a negative population reactive with *T. cruzi* LPPG is shown along the vertical axis while the Signal to Negative ratio (S/Neg) is shown along the horizontal axis of the graph, wherein the number of sera tested was 289.
Figure 2A:
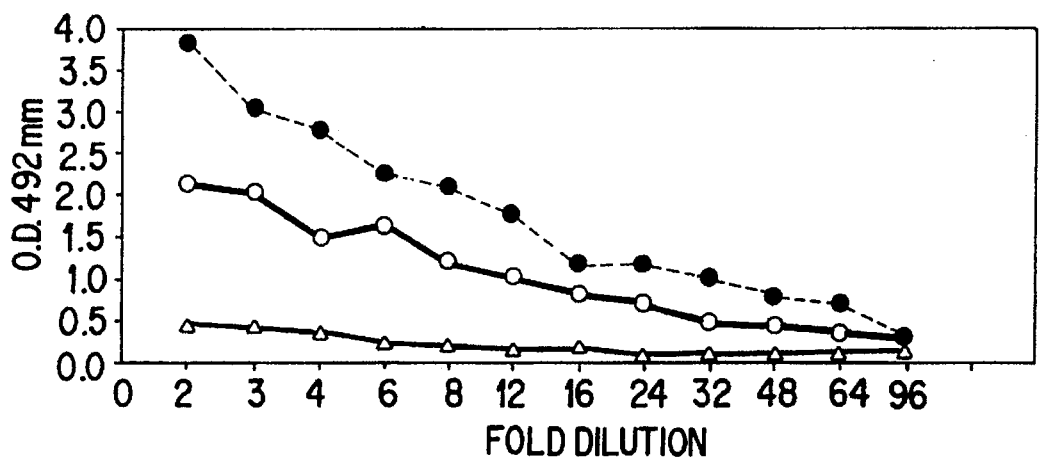
FIGS. 2A through 2D show the results of the assay of the invention graphed as a function of Optical Density (OD) versus the dilution factor of the (previously positive) tested sera, wherein a solid circle indicates gp90 bead, an open circle indicates gp60/50 bead, and an open triangle indicates LPPG-BSA bead.
Figure 2B:
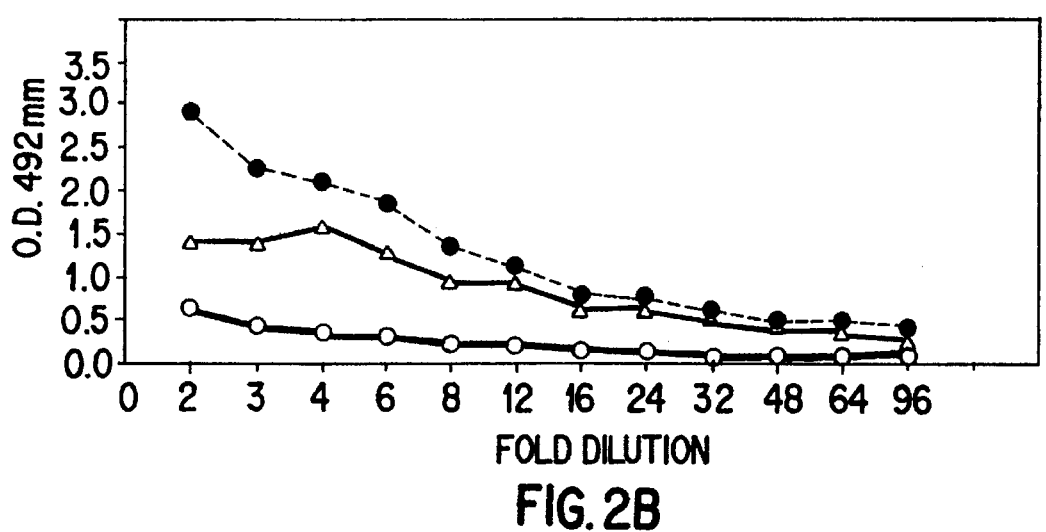
Figure 2C:
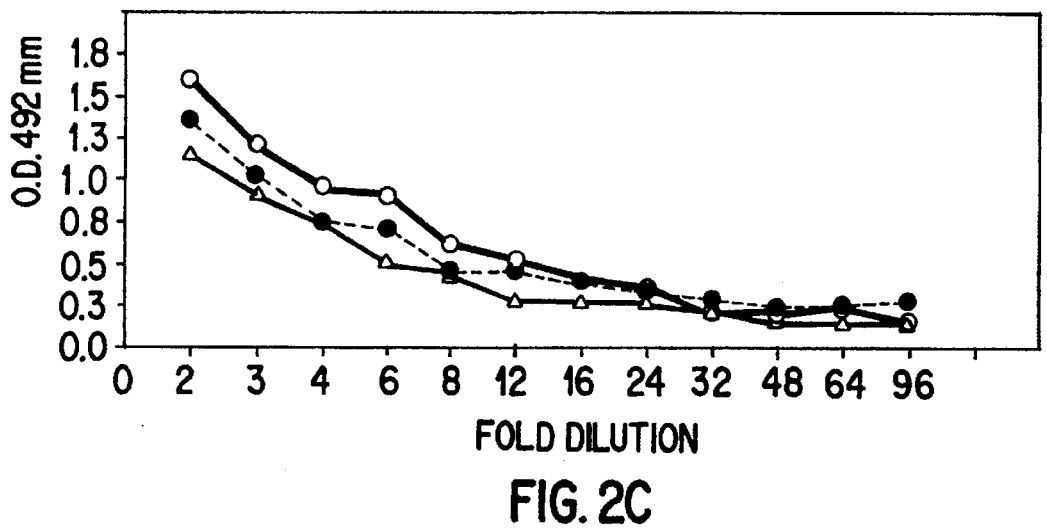
Figure 2D:
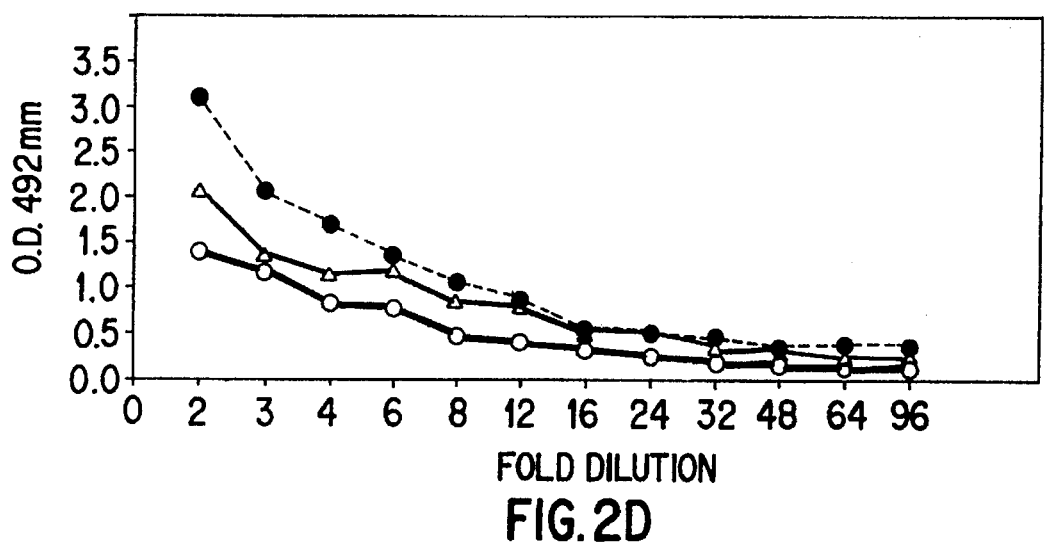

*Sensitivity (%) = (No. Chagas-EIA Positive/No. Xenodiagnosis Positive) × 100;
**Consensus Positive are reactive by Hemagglutination and Immunofluorescence assays Two hundred eighty-fine negative samples from a "low risk" region (southeast Wisconsin) also were assayed by the confirmatory EIA. As seen in FIG. 1A, FIG. 1B and FIG. 1C, the two hundred eighty-four samples were below the cutoffs in at least two of the three kinds of antigen-coated beads. Five samples demonstrated an absorbance value (S/N) above the cutoff in one of three beads. However, since confirmation is determined by reaction above the cutoff values in at least two of three beads, the overall performance of the confirmatory assay of the invention was 100% (289/289).

Confirmatory EIA of Xenodiagnosis-Positive Samples

A sample positive by xenodiagnosis represented a sample in which there was a greater degree of certainty as to an individual having Chagas' Disease and thus, antibody to T. cruzi. Table 1 summarizes the data on the confirmatory assay of the invention on these samples. As the data from the Table 1 demonstrate, all samples showed an absorbance above the cutoff value with three-of-three or two-of-three beads. No samples had to be retested by RIPA. The overall agreement on the confirmatory assay was 100% (28/28) on xenodiagnosis-positive samples.

Evaluation of the Three-Bead Confirmatory Assay with a Dilution Panel

The assay of the invention was tested with four consensus positive samples diluted two- and three-fold from 1:2 to 1:96. The results of these tests are shown in FIG. 2A, FIG. 2B, FIG. 2C and FIG. 2D. As can be seen in THIS FIGURE, all of the sera tested were positive (above the cutoff value in at least two of three antigen beads) by the confirmatory assay of the invention through a dilution of 1:16. The samples were considered consensus positive when tested by the Chagas US Screen EIA (Abbott Laboratories, Abbott Park, Ill.), hemagglutination and indirect immunofluorescent antibody. All samples were diluted two- or three-fold to a dilution of 1:96.

Cross-Reactivity

Specimens from patients with other parasitic diseases were tested with the confirmatory assay of the invention. As the data in Table 1 demonstrate, absorbances were below the cutoff value, which indicated no cross-reactivity in the assay.

Evaluation of Three-Bead Confirmatory Assay with Samples from the U.S. Prevalence Study In an in-house evaluation, 13,109 blood samples donated in southwestern areas of the U.S. were screened with a Abbott Chagas Antibody EIA (Abbott Laboratories, Abbott Park, Ill.). All samples with signal-to-negative (S/N) greater than 3.0 were assayed by the confirmatory assay of the invention as detailed in Example 5. Thirty-four (34) samples in the screening assay were "RR" (repeat reactive). As seen in Table 2, nine (9) samples were positive in at least two-of-three beads, two samples were positive in one-of-three beads, and two samples were negative on all three beads. Four samples (two negative on all three beads and two positives on only one bead) were indeterminate and required additional analysis by RIPA.

TABLE 2

Confirmatory Assay of the Invention Tested with Positive Sera

| | Positive Sample Type | | |
|---|---|---|---|
| | Xenodiagnosis | Consensus* | In-House Study |
| Confirmatory Assay Results | | | |
| 3/3 Positive | 21 | 56 | 7 |
| 2/3 Positive | 7 | 24 | 2 |
| 1/3 Positive | 0 | 2 | 3+ |
| 0/3 Positive | 0 | 0 | 2+ |

*Samples in which Hemagglutination and Immunofluorescence Assays were positive in both tests
+Samples to be confirmed by RIPA RIPA FIG. 3 represents the results of a RIPA of 125I-labeled solubilized membrane extract of epimastigotes of *T. cruzi* with the dilution panel of positive sera for antibody to *T. cruzi*. Nine (9) major proteins were revealed under reducing conditions; these bands had molecular weights (Mr) of 19, 25, 28, 32, 34, 44, 58, 69 and 90 kD (kilodaltons). There appeared to be two (2) bands of Mr 32 and 34 kD which were strongly precipitated, while the 90 kD band was of medium intensity; these three bands appeared to be the most diagnostic proteins. The 19 and 25 kD bands appeared to be dependent on the titer of serum, being present in the positive control 1:22, 1:100, 1:4 (high positive); and the screening test's positive control (previously described above). The 19 and 25 kD bands were absent in the 1:6 (mediium positive); 1:9 (borderline positive); 1:13.5 (low positive); 1:22 (non-reactive positive); and the negative control for the Chagas' Disease screening assay previously described herein. The bands which immunoprecipitated at 28, 44, 58 and 69 kD appeared in various negative samples tested and were non-specific. As demonstrated, the 32, 34 and 90 kD bands appeared in all of the dilutions tested.

Comparison of RIPA to Xenodiagnosis-Positive Samples

All 28 xenodiagnosis-positive samples were analyzed by RIPA. All samples showed the characteristic diagnostic bands at 32, 34 and 90 kD. Several of these sera also demonstrated high titer bands at 19 and 25 kD. The overall agreement on the RIPA was 100% (28/28) on xenodiagnosis-positive samples.

RIPA of Samples from U.S. Prevalence Study

To demonstrate the utility of RIPA, 122 samples from the U.S. prevalence study described above with signal/negative (S/N) greater than 3.0 were assayed as follows. Samples with S/N from 3.0 to 5.0 (N=100) were negative in RIPA. As Table 3 below demonstrates, of the 22 samples having S/N greater than 5.0, 13 samples were confirmed positive. Four of the five indeterminate samples from the confirmatory assay confirmed positive, and one sample remained indeterminate. Seven (7) samples demonstrated bands at 19 and 25 kD, which indicated high titer sera.

TABLE 3

Comparison of the 3-Bead Assay Versus RIPA

| | 3-BEAD ASSAY RESULT | | | | RIPA |
|---|---|---|---|---|---|
| Sample Type | 3 of 3 | 2 of 3 | 1 of 3 | 0 of 3 | Positive |
| Xenodiagnosed Positives | 21 | 7 | 0 | 0 | 28 |
| Consensus Positives | 56 | 24 | 2 | 0 | 82 |
| In-House US Field Study | 7 | 2 | 3 | 2 | 13 |

As shown by the data presented above, both the confirmatory assay of the present invention and RIPA had a clinical sensitivity of 100% when tested against xenodiagnosis-positive sera. When tested with consensus positive sera, the confirmatory assay of the invention had a sensitivity of 97.56% (80/82). The remaining 2.4% (2/82) showed reactivity with one of the three beads. When assayed against negative samples from a "low risk" region of southeast Wisconsin, the confirmatory assay of the invention had a specificity of >99.99%. The proposed scheme for confirmation is shown in FIG. 3. Thus, it can be seen that test samples reactive with two-of-three or three-of-three *T. cruzi* antigens is considered a confirmed reactive seropositive sample. If the absorbance of a sample is only above the cutoff value in one of the three antigens, or the sample is not above a cutoff with all three antigens, the sample is considered as negative, or it is subjected to RIPA. In RIPA, test samples are confirmed reactive when three-of-three or two-of-three diagnostic bands precipitate. Samples immunoprecipitating only one band are considered indeterminant, and samples which do not immunoprecipitate any bands are considered negative. The confirmatory assay of the invention provides a means of reducing the number of samples which need to be assayed by RIPA. This is beneficial because RIPA is considered a very time-consuming and labor-intensive procedure when compared to the assay of the present invention: the confirmatory assay of the invention requires approximately two hours to perform, while a RIPA may take upwards of ten days for a result. RIPA previously has been used to confirm the presence of *T. cruzi* antibody, wherein a protein extract of surface radiolabeled parasites was used when testing pedigreed reactive samples. Protein bands at 72 and 90 kD in RIPA appeared to be sensitive and specific. These antigens appeared to be highly conserved across a wide geographical selection of strains of the parasite. However, RIPA has practical limitations in that radioisotopes with short half-life are used, the technique is time-consuming, and the technique is not readily adaptable to large scale screening. R. C. K. Wong et al., *Trans. R. Soc. Trop. Med. Hyg.* 80:275–281 (1986).

It is contemplated that the assay of the invention can be optimized even further by varying assay conditions and/or incubation times, using various combinations of antigen or antibody capture or probe reagents, and other methods, reagents and conditions known to those skilled in the art. The variance of the antibody capture reagent may then require the use of a different antigen capture reagent. All these variations are contemplated to be within the scope of this invention. Also, while some of the assays described in the examples used an automated system, it is well within the scope of the present invention that manual methods or other automated analyzers can be used or adapted to the assay of the present invention. Therefore, the present invention is meant to be limited only by the appended claims.

What is claimed is:

1. A Gp60/50 antigen made by a process comprising:

a. isolating the membrane of the epimastigote stage of *T. cruzi* by dounce homogenization;

b. extracting the Gp60/50 antigen;

c. applying the resultant extract of step (b) to a *Galanthus nivalis* lectin affinity column and eluting with a carbohydrate;

d. purifying the eluate with an affinity column comprising a monoclonal antibody specific for Gp60/50.

* * * * *